United States Patent [19]  
Meier

[11] Patent Number: 4,669,878  
[45] Date of Patent: Jun. 2, 1987

[54] AUTOMATIC MONOCHROMATOR-TESTING SYSTEM

[75] Inventor: Daniel J. Meier, Indianapolis, Ind.

[73] Assignee: American Monitor Corporation, Indianapolis, Ind.

[21] Appl. No.: 876,658

[22] Filed: Jun. 18, 1986

Related U.S. Application Data

[63] Continuation of Ser. No. 626,292, Jun. 29, 1984, abandoned.

[51] Int. Cl.⁴ .......................... G01J 3/18; G01J 3/42
[52] U.S. Cl. ................................ 356/319; 356/334; 364/498; 422/67; 422/68; 436/43; 436/164
[58] Field of Search ............... 356/319, 320, 326, 328, 356/331–334, 329, 418, 419, 432, 436, 244, 246; 364/497, 498; 422/67, 68; 436/43, 164

[56] References Cited

U.S. PATENT DOCUMENTS

| Re. 28,803 | 5/1976 | Durkos et al. ............... 235/151.3 |
|---|---|---|
| 2,621,298 | 12/1952 | Wild et al. .................. 356/319 |
| 3,431,054 | 3/1969 | Doonan et al. ............... 356/334 |
| 3,901,656 | 8/1975 | Durkos et al. ................ 23/230 |
| 3,972,617 | 8/1976 | Shibata et al. ............... 356/319 |
| 4,322,166 | 3/1982 | de Mey, II ................... 356/334 |
| 4,412,744 | 11/1983 | Lee et al. .................... 356/319 |
| 4,454,472 | 6/1984 | Moore ....................... 324/158 R |
| 4,456,380 | 6/1984 | Kondo et al. ................ 356/418 |

FOREIGN PATENT DOCUMENTS

| 97644 | 6/1983 | Japan ......................... 356/246 |
|---|---|---|
| 2014305 | 8/1979 | United Kingdom ............ 356/409 |
| 2096347 | 10/1982 | United Kingdom ............ 356/319 |

OTHER PUBLICATIONS

Karjalainen et al., Journal of Physics E, vol. 7, No. 4, Apr. 1974, pp. 241-243.
Papadakis et al., Analytical Chemistry, vol. 47, No. 9, Aug. 1975, pp. 1644-1649.
Collins, Journal of Physics E, vol. 8, No. 12, Dec. 1975, pp. 1021-1023.
Defreese et al., Analytical Chemistry, vol. 48, No. 11, Sep. 1976, pp. 1530-1536.

Primary Examiner—F. L. Evans
Attorney, Agent, or Firm—Willian, Brinks, Olds, Hofer, Gilson & Lione

[57] ABSTRACT

An automated chemistry-testing system for analyzing serum samples in which a controlled intensity, monochromatic light beam of substantially any desired wavelength can be selectively directed through any one of a plurality of test solutions in a spectrophotometer. The system operates at very high speed, permitting serum test solutions to be scanned with a multiplicity of wavelengths of light to provide extensive data on the characteristics of the serum. The invention also provides substantial flexibility and permits a wide variety of test to be more reliably performed.

32 Claims, 5 Drawing Figures

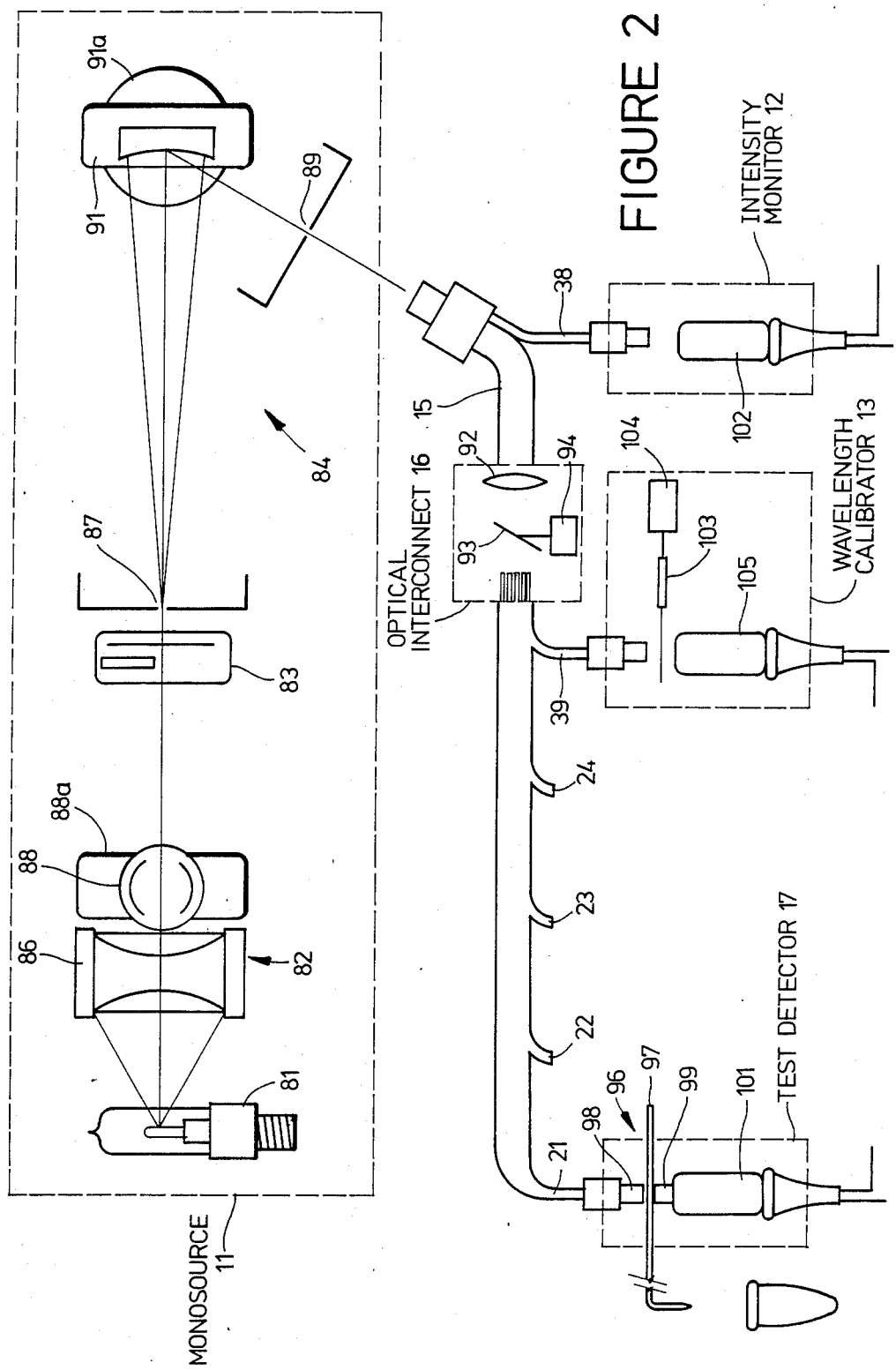

AUTOMATIC MONOCHROMATOR-TESTING SYSTEM

This application is a continuation of application Ser. No. 626,292, filed June 29, 1984, now abandoned.

BACKGROUND OF THE INVENTION

The present invention relates generally to a monochromator-testing system and method, and, more particularly, to a monochromator-testing system and method for use in an automated chemistry-analyzing system for analyzing blood or other body fluids.

The chemical analysis of blood or other body fluids or serums is a vital part of medical diagnosis. Testing for various serum constituents, such as glucose or heart enzymes, for example, or for some other medically significant factor, can be performed in a manual or automated process by adding specific amounts of various reactive chemicals or reagents to a sample of the serum in a specific sequence and under specified conditions of temperature and time. The light-transmittance value of the resulting test chemistry is then measured, and this value can be used to determine the amount of the particular constituent being measured in the serum. The term "serum" is used to designate any biological fluid.

More specifically, in analyzing a serum specimen, a sample of the specimen is typically placed in a test tube or other appropriate container; and one or more specific reagents are added, depending upon the particular test to be performed. When the required chemical reactions have taken place, a sample of the completed test chemistry is removed from the test tube; and the light-transmittance value of the test chemistry is ascertained by using a spectrophotometer or the like. This value can be used to calculate the optical density of the chemistry; and from this, the concentration of the constituent of interest in the serum can be ascertained. Automatic systems for performing such analyses are disclosed, for example, in U.S. Pat. No. 3,901,656 and No. Re. 28,803.

Determination of the concentration in a serum specimen of constituents of interest requires determination of the optical densities of the serum solutions and the test chemistries. This determination is made by passing light of a selected wavelength or wavelengths through samples of the serum solutions and test chemistries to measure their light-absorbance values at the selected wavelength or wavelengths. The terms "optical density" and "light absorbance" are used synonymously to describe the effect of the test solution on light that passes through it. Light transmittance may also be used to describe serum solution testing. Correct results require accurate determinations of the light-absorbance values of the serum solutions and test chemistries. A variety of factors can interfere with the accuracy of these determinations. For example, the presence of bubbles in the test solution can cause measurement errors. Similarly, factors, such as turbidity or settling, can also interfere with the accuracy of the measurements.

Moreover, a number of constituents normally present in varying amounts in the serum itself may introduce significant errors into the measurements. These endogenous transferring substances include bilirubin, hemoglobin, lipids, and the like. Such substances absorb light at various specific wavelengths; and when the maximal absorbances of the interfering substances are at wavelengths close to those wavelengths at which the test chemistries are to be measured, the optical measurements will be severly affected unless corrected or compensated for in some way.

Techniques have been developed to reduce the effect of these interferences with the accuracy of the measurements. For example, where the effect of the interference on the optical density of a solution is known to be significant in one range of wavelengths and nominal in others, several measurements of the same test solution may be taken at different wavelengths. One or more wavelengths may be selected to provide a measure of the significant determination of an interfering factor without a significant contribution from the factor being measured by the test chemistry. Other wavelengths may be selected to provide a significant determination of the factor being measured by the test chemistry with relatively nominal interference. From such data, the contribution of the interference may be determined and compensated for in analyzing the test results.

Such techniques have generally been limited to manual laboratory procedures practiced by trained technicians, although some automatic serum chemistry-analyzing machines have the limited capability of practicing such techniques with a few selected wavelengths. In such systems, this has been accomplished by providing a plurality of filter elements and selectively inserting them into the light path. Such systems are limited to only a few light wavelengths and provide little flexibility.

Where the system is capable of generating data at only a few wavelengths within the milliseconds that represent substantially the same time for data comparison and use, the few data points, while providing a measure of the characteristics of a serum solution and test chemistry at the wavelengths of data points, provide no reliable information on the light-absorbance characteristics of serum solution and test chemistry between the data points. Isolated data points cannot be used to reliably establish whether the light absorbance is increasing or decreasing with varying wavelength adjacent the data points and, of course, can provide no information on the rate of change of any such variation. Three data points, for example, may appear to lie on a straight line that represents constant light absorbance as a function of wavelength when the light absorbance actually varies substantially and significantly between the data points. Determination and use of reliable information on such variations were not possible in automatic serum chemistry testing systems.

Such systems have also used an intense polychromatic ("white") light passing through the test solution. Such intense polychromatic light includes wavelengths that can effect changes in the serum constituents, the reagents, and the test chemistry.

SUMMARY OF THE INVENTION

The present invention provides an automated, chemistry-analyzing apparatus in which a controlled intensity, monochromatic light of substantially any desired wavelength can be selectively directed through any one of a plurality of test solutions in a spectrophotometer. A virtually unlimited variety of tests can be performed on the test solutions. The test chemistries can be scanned with substantially monochromatic light from a wide range of wavelengths in a very short period of time to provide data at a multiplicity of wavelengths. With such data, the serum characteristic as a function of wavelength and its derivatives can be reliably determined and used to correct test data for interferences and to identify invalid tests. In referring to such a multiplicity of wavelengths, I mean more than about 10 to about 20 wavelengths and as many as 250 wavelengths in a number of tests.

A presently preferred embodiment includes means for providing substantially monochromatic light of substantially constant intensity having any selected wavelength from about 300 nanometers to about 800 nanometers. The optical system of such means comprises a monochromator which includes a light source generating a beam of polychromatic light and a diffraction grating to produce substantially monochromatic light of different wavelengths. Substantially monochromatic light means light having a very narrow range of wavelengths, typically 3–4 nanometers. The grating is rotatable; and by rotating the grating, a beam of substantially monochromatic light of any selected wavelength may be generated and directed to a test solution to be evaluated.

The means for providing substantially monochromatic light also comprises intensity-controlling and calibrating means. The intensity-controlling means insures that the monochromatic light beams will be of substantially constant intensity at all real times and at all wavelengths. Such means comprises apparatus for monitoring the light intensity at each wavelength, and a variable aperture optical system that is adjusted in real-time to control the intensity of the polychromatic light directed to the diffraction grating and, hence, the intensity of the selected monochromatic light separated therefrom.

The calibrating means insures that the selected wavelength of light will be produced when it is desired. The preferred calibration means includes a holmium oxide filter through which monochromatic light of each available wavelength and constant intensity is sequentially passed. By producing a series of signals that represent the absorbance of the filter at each wavelength, and by comparing this series of signals with the known absorbance characteristics of the holmium oxide filter, the grating position can be correlated with the wavelengths that it produces; and a reliable selection of monochromatic light is possible.

Fiber-optical pathways are provided in the system for directing the light beam from the monochromator to each of a plurality of flow cells containing test solutions to be evaluated. The fiber-optical pathways permit the direction of substantially monochromatic light to a plurality of flow cells at one time. By addition of an optical "multiplexer", as part of the optical interconnect system, substantially monochromatic light of different selected wavelengths can be directed to different flow cells at any time to permit measurements to be taken. The light absorbance of the test solutions is measured, preferably with the photomultiplier tubes at each flow cell.

The system includes multiple microprocessors to control the methods of system operation and testing. The control processor provides control over the mechanical components of the system and adjustment of the system electronics. The control processor provides periodic calibration of the monochromator means and test chemistry light measurement means. The control processor also provides a program for installation of the system and for periodic component checking and alignment. The control processor stores the characteristics of important replaceable system components and permits the system to be realigned in the event the components must be replaced.

Testing methods are controlled by a separate microprocessor which can store the methods of 30 test chemistries. The testing methods of selected test chemistries are transferred to the control processor, which runs the system to perform the tests. The multiplicity of resulting data from the tests is transferred to the testing microprocessor for analysis and determination of serum characteristics as a function of wavelength.

The system of the present invention operates at very high speed, permitting serum test solutions to be scanned with a multiplicity of wavelengths of light to provide extensive data on the characteristics of the serum. The invention also provides substantial flexibility and permits a wide variety of tests to be more reliably performed. Further details and advantages of the invention will become apparent hereinafter in conjunction with the detailed description of the preferred embodiments.

BRIEF DESCRIPTION OF THE DRAWINGS

FIG. 2 schematically illustrates the nonelectronic portion of the system of FIG. 1.

DETAILED DESCRIPTION OF THE PREFERRED EMBODIMENT

Figure 1:
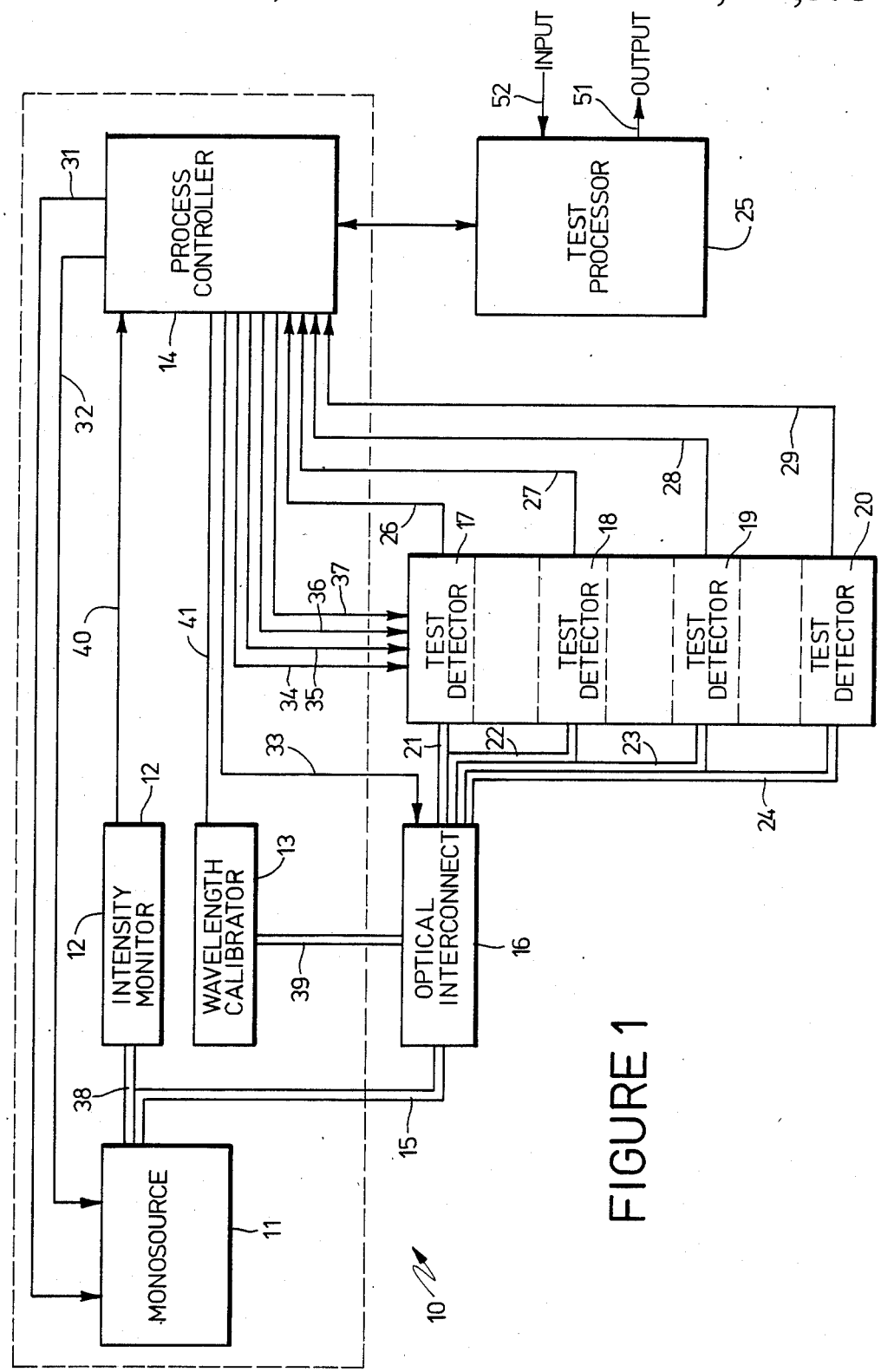
FIG. 1 illustrates an overall block diagram of a preferred embodiment of the invention.

FIG. 1 illustrates an overall block diagram of a preferred system of this invention. The system includes a means 10 to provide substantially monochromatic light of substantially constant intensity at any selected wavelength from about 300 nanometers to about 800 nanometers. Means 10 includes a monosource 11, an intensity monitor 12, a wavelength calibrator 13, and control processor 14 of the system electronics. Means 10 generates a substantially monochromatic beam of light at essentially any selected wavelength. This monochromatic light beam is directed via fiber-optical pathway 15 to an optical interconnect system 16, which directs the light beam to one or more detectors, for example, 17, 18, 19, 20, via fiber-optical pathways, for example, 21, 22, 23, 24. The test detectors are capable of presenting a particular test chemistry or serum solution to be analyzed in the substantially monochromatic light. In particular, as will be described later in greater detail, the system is designed to permit up to four different test solutions to be analyzed simultaneously in four separate spectrophotometers; and the optical-interconnect system 16 can direct a beam of light of a different selected wavelength to each of the four test solutions.

The system electronics of FIG. 1 includes, in addition to the control processor 14 for generally controlling the operation of the various components of the optical-illumination system, electronics for analyzing the detector outputs, for example, 26, 27, 28, 29. Microprocessor 25 may produce an output 51 indicating the results of the test being conducted and may be instructed by any conventional data input system or other computer 52 upon the tests to be conducted. The system electronics, through the control processor 14, has the capability of controlling the operation of the monosource 11 via lines 31 and 32, the optical interconnect 16 via line 33, and the test detectors 17–20 via lines 34, 35, 36, and 37. The control of these components is described later in greater detail.

As shown in FIG. 1, the intensity monitor 12 is coupled to the monosource 11 via fiber-optical pathway 38 and the wavelength calibrator 13 is coupled to the optical interconnect 16 via fiber-optical pathway 39. The function of the intensity monitor 12 is to monitor the intensity of the light from the monosource and develop signals to maintain the monochromatic light beam at a substantially constant intensity notwithstanding its wavelength. The function of the wavelength calibrator 13 is to calibrate the monosource which generates the monochromatic beam of light to insure that the selected wavelength of light will be produced when desired. The signal outputs of the intensity monitor 12 and the wavelength calibrator 13 are transmitted to process controller 14 by lines 40 and 41, respectively. The signals on lines 40 and 41 are developed into driving outputs to control the monosource via lines 31 and 32.

FIG. 2 schematically illustrates the various components of the preferred means to provide substantially monochromatic light of substantially constant intensity. As shown in FIG. 2, the monosource 11 is comprised of a plurality of components including a source 81 of polychromatic light, a variable aperture system 82, an order filter 83, and a monochromator, generally designated by reference numeral 84. The polychromatic light source 81 preferably comprises a Halogen lamp of conventional type. Light from the Halogen lamp is received by variable aperture system 82. The variable aperture system includes a collimating lens system 86 to concentrate the light at the entrance slit 87 of the monochromator 84 and a variable aperture 88. The aperture structure includes a shutter system which is driven by a galvanometer movement 88a to maintain the monochromatic beam of light at a constant intensity notwithstanding its wavelength by varying the intensity of the polychromatic light beam directed at the monochromator 84. After passing through the variable aperture system 82, the polychromatic light beam then passes through order-separation system 83. The system is controlled by a rotary solenoid and comprises two order-separation glasses. The rotary solenoid rotates one or the other of the two glasses in the light path. The operating range for one of the glasses is preferably from about 300 to about 500 nanometers, while the other glass has an operating range of from about 400 to about 800 nanometers. There is some overlap of the bandwidth due to the test chemistries. Either one glass or the other glass is in the light path, allowing either 300 to 500 nanometer light or 400 to 800 nanometer light to pass through. Selection of the glasses is handled automatically upon identification of the test to be conducted.

After passing through the order-separation glasses, the light enters the monochromator 84 which includes an entrance slit 87, an exit slit 89, and a diffraction grating 91. The grating 91 is mounted on and rotated by a galvanometer movement 91a. The grating is used to separate different wavelengths of light from the light entering the entrance slit 87. When incident light strikes the grating, different wavelengths will be reflected from the grating at different angles (the angle is determined by the wavelength). By rotating the grating 91, substantially monochromatic light of different wavelengths within the spectrum of the polychromatic light beam can be directed to the exit slit 89 of the monochromator. The galvanometer 91a, which is like a meter movement but more massive, can rotate the grating 91 through a range of angles and scan the spectrum of the polychromatic light across the exit slit 89 of the monochromator, producing a multiplicity of substantially monochromatic light beams. The grating is enclosed and sealed in a housing to prevent the entry of dust which can destroy its background characteristics (i.e., light is scattered by striking dust particles, thereby increasing background radiation which affects the linearity of the measurement system). It is imperative to have as little background radiation as possible, particularly because of the higher absorbance readings that may be accommodated with this system. The grating itself is capable of separating light into wavelengths of about three nanometers; and the term substantially monochromatic, as used throughout this application, therefore, is intended to comprise a light having a spectrum width of approximately three nanometers.

Thus, with the system of this invention, it is possible to generate substantially monochromatic light of substantially any wavelength within the range of from about 300 to about 800 nanometers as passed by the order-separation glasses. From the exit slit 89 of the monochromator 84 (i.e., the output) of the monosource 11, the light impinges upon a bifurcated optical fiber bundle. Approximately, 20 percent of the light is directed to intensity monitor 12 via fiber-optical pathway 38 where it is used to monitor the intensity of the monochromatic light. About 80 percent of the light goes to optical interconnect 16 via fiber-optical pathway 15. The reason for the 20/80 split is to provide substantially equal light to the test detectors and wavelength calibrator notwithstanding any loss of light in the light-directing system. The test detectors 17-20 use, preferably, photomultiplier tubes to determine light absorbance of the test solutions, and it is advisable that the light intensity be substantially constant at each photomultiplier tube to obtain similar gain and response time.

As mentioned above, the intensity monitor 12 monitors the intensity of the monochromatic light passing through optical fiber 38 to maintain substantially constant intensity monochromatic light for transmission to the test detectors 17-20 and the wavelength calibrator 13. Intensity control of the monochromatic light emanating from the monosource 11 is effected by controlling in real time the variable aperture 88 in the path of the polychromatic light leaving the light source 81. Basically, the monochromatic light passes through fiber-optical pathway 38 and is sensed by photomultiplier tube 102. The photomultiplier tube 102 generates a signal which is a function of the light intensity. This intensity signal is delivered on line 40 to the process controller 14. The process controller 14 then develops a driving signal which is delivered over line 31 to the galvanometer movement 88a which operates the shutter mechanism of the variable aperture means 88. The variable aperture means 88 thereby adjusts the intensity of the polychromatic light beam in real time to maintain a constant intensity monochromatic light output at all wavelengths within the 300 to 800 nanometer spectrum of the polychromatic light.

The optical interconnect 16 may be a direct optical coupling of 80 percent of the substantially monochromatic light to the four fiber-optic pathways 21-24 in a manner known in the art. Another embodiment of an optical interconnect, shown schematically in FIG. 2, includes an "optical multiplexer".

The optical interconnect multiplexer of FIG. 2 includes a lens assembly 92 connected to the input fiber 15 from the monosource, a mirror 93 mounted to a stepper motor 94, four optical fiber transmitters 21-24 going out to the test detectors 17-20, and one optical fiber transmitter 39 going to the wavelength calibrator 13. The function of the mirror 93 is to direct the light beam from the monochromator 84 to each of the four output optical fibers 21-24 and to the optical fiber 39. Alignment of the optical interconnect mirror is performed by system-generated software. When the optical interconnect system 16 is first initialized, the stepper motor steps to the "home" position at the optical fiber 39. "Home" position is indicated generally by a reference sensor on the sensor disk, which is actually about two to three motor steps wide so that it is easy to find. Alignment is completed by moving in half steps to locate the maximum light intensity on the optical fiber 39. Once the mirror is aligned with "home" position, the process controller calculates the number of steps to each of the other optical fibers. Actual motor alignment is accomplished automatically every time the system is initialized.

The wavelength calibrator 13 insures that the desired wavelength of light will be passed through the exit slit 89 when called for. A holmium oxide calibration filter 103 is used to calibrate the monochromator 84. Holmium oxide glass has a very complicated light absorbance spectrum with a number of absorbance peaks and valleys at known wavelengths. The entire spectrum of polychromatic light can be "fingerprinted" using this holmium oxide filter. The calibration filter 103 is mounted on a solenoid 104, which, when activated, puts filter 103 in the path of the light from optical fiber 39 when the monochromator 84 is to be calibrated. In calibrating the monochromator 84, the calibrating filter is placed between the optical fiber 39 and photomultiplier tube 105 of the wavelength calibrator 13. The grating is then rotated by the galvanometer movement 91a to scan the full spectrum of constant intensity monochromatic light (i.e., from about 300 nanometer wavelength through about 800 nanometer wavelength) at the output 89 of the monochromator 84. The photomultiplier tube 105 generates a signal from each wavelength that represents the absorbance of the holmium oxide filter at that wavelength. The set of signals are transmitted to the process controller 14 over line 41. The process controller, pursuant to the calibration program, compares this signal data with stored data on the light-absorbance spectrum of the holmium oxide filter 103 to correlate the wavelength of the monochromatic light with the rotational position of the grating 91 of the monochromator 84. The rotational positions of the grating 91 are then stored for a multiplicity of wavelengths in the 300 to 800 nanometer spectrum. In operation, for example, if light at a wavelength of 340 nanometers is requested, the process controller 14 can determine from the stored calibration data the position to which grating 91 must be driven so that light of that wavelength will leave exit slit 89. The monochromator 84 can be calibrated with a single pass through the spectrum. After the calibration is completed, another pass is generally made based on the calibration to verify its accuracy by matching the original table. This calibration procedure is part of an alignment protocol for the system every time the instrument is powered up and before every test, once every 7.2 seconds.

In testing serum samples and test chemistries, monochromatic light of selected wavelength is directed by the optical interconnect 16 on one or more of the desired fiber-optical pathways 21-24 and is directed to one or more test detectors 17-20 which comprise essentially spectrophotometers. More specifically, the test detector 17 includes a housing 96 which contains a flow cell 97, an input optical fiber 98, and an output optical fiber 99. The light from the output optical fiber 99 is received by a photomultiplier tube 101 which is supported within a housing with the photomultiplier tubes of the other test detectors and the photomultiplier tubes for the wavelength calibrator and the intensity monitor. In FIG. 2, however, the photomultiplier tubes are separated for the purpose of clarity. The flow cell 97 is designed to be customer replaceable. Specifically, each flow cell has a number etched on its side, which number is a calculation of the actual light path length through the flow cell. This number is entered into the process controller 14 of the system electronics. The path length of the flow cell is stored because a correction is made for the different path lengths of each photocell. With this information stored, the raw data that comes out of the measurement system is automatically corrected to minimize error. The correction calculations are done in a mathematical process within the process controller 14. The path length of the flow cell is defined by in-house testing. Specifically, a standard flow cell, kept in-house, is used as a reference; and all other flow cells are compared with the standard flow cell to provide for the system a light path length for every photocell based on the reference number placed on it.

The photomultiplier tubes or PMTs used in this system are small and have a very fast response time (faster than a silicone detector) in the order of nanoseconds due to their very low internal capacitance. Although the sensitivity of the photomultiplier tubes will deteriorate with time, the deterioration can be compensated for through appropriate software by adjusting the high voltage to maintain a proper gain. This procedure will prolong the life, which can be a couple of years with this compensation, of the photomultiplier tubes. A shutter is preferably provided in the front of each PMT to protect the PMT from direct ambient light if an optical fiber is disconnected while there is power to the PMT and also to provide dark current testing. Since the flow cells are replaceable, when an optical fiber is pulled from one of the housings and a high voltage (typically 650 volts) is applied to the PMT, ambient light conditions or any other light source can be high enough to overload the PMT, degrading them or severely burning the plates out, making the PMT inoperable.

Dark current is also a common phenomenon of a PMT. Dark current drifts quite a bit; even ambient temperature is enough to cause drifting. Because of the need to use logarithmic amplifiers, even a small change in dark current can produce a significantly erroneous output signal. In order to compensate for this phenomenon, a test is performed to determine the dark current of the photomultiplier tubes every 1.5 seconds in order to recorrect or rezero the logarithmic amplifiers so drift error is eliminated.

The shutters are solenoid controlled and mounted on top of the PMT housing. A set of comparators in the measurement system monitors the preamplifiers for the photomultiplier tubes. If the output of any one of the preamplifiers exceeds about 10.5 volts, which is the limiting factor, it will automatically trigger the comparator and activate the shutter to close. This protective action is accomplished by software within process controller 14. Upon "power down", the shutters are in the normally closed position.

The process controller 14, which controls the operation of the components of the monosource, the optical interconnect, the intensity monitor, the wavelength calibrator, and the test detectors, is, for example, an Intel 8024 microprocessor which has an 8085A-2 central processing unit. In addition to the process controller 14, the system electronics to control the optical components includes an analog processor unit (APU) with a high-voltage supply, a data acquisition unit (DAU), two general control units (GCU), and a fluorometer control unit (FCU) and associated high voltage supply. These four units are all software controllable.

The analog processor unit (APU) is an analog system that takes the inputs from the test and intensity-monitoring photomultiplier tubes, transforms the signals to current, and amplifies them in a three-stage amplifier. The test analog signals are manipulated through software by programmable gain and offset circuitry. The test and intensity-monitoring signals perform two different functions. The signals go from the photomultiplier tube module to the data acquisition units. The signals are also multiplexed, amplified, and fed to a difference amplifier which then transfers the resulting signal to the data acquisition unit. The signals are also fed into two comparator circuits which determine if the shutters of the PMT tubes need to be closed because of exposure to an overload of bright light (ambient or otherwise).

The data acquisition unit (DAU) contains a 16-channel multiplexer which is used to take the analog signals from the analog processor unit (Test, Intensity Monitoring, Difference signals and analog ground), and other inputs for system diagnosis. These signals are multiplexed together and sent through an anti-aliasing filter, which filters out other noise and quickly throughputs the analog data, onto a 16-bit A/D Converter. The signals are then presented to the data buss for software interpretation. The two shutter control signals from the analog processing unit are carried through to the data buss. A thermistor input is used for flow cell temperature. There are also four expansion or auxiliary inputs to the multiplexer. Two of the channels are voltage inputs from Ion Specific Electrodes. When the system tests a solution using the Ion Specific Electrodes, it is programmed to read those devices in order to obtain their output values. The other two channels are for future expansion.

The measurement system has the capability of reading percent Transmittance (% T) as well as logarithmic output or Absorbance (ABS). These two references reside within the data acquisition unit. There is another internal reference within the data acquisition unit which is used to check the scaling of the A/D Converter to see if it is accurate. The A/D Converter has banked in +15 volts or −15 volts to guarantee that all the bits to the A/D Converter operate. The +5 volts line and the absolute values of each of the other connected power supplies are checked. The voltage ranges of each power supply are stored in the process controller 14, and a faulty power supply can be detected by measuring power supply voltage through the A/D Converter.

The general control units (GCUs) contain the current drivers for the scanner (grating 91 on the galvanometer 91a) and the variable aperture (the shutter on the galvanometer). The general control units also contain the drivers that control the stepper motor for the mirror on the multiplexer (optical interconnect) and, in one of the GCUs, the drivers for the order-switching, calibration glass and shutter solenoids. There are also sensor inputs; two are from the sampler stepper motor sensor disk.

The fluorometer control unit (FCU) consists of a unit for controlling the filter wheel, shutter solenoid for the Test photomultiplier tube, lamp power supply and CW light source for the fluorometer. The FCU has a set of discriminator photon counters that it uses for the photon counting mode, and other supporting fluorometer electronics.

The analog processor unit, data acquisition unit, general control units, and fluorometer control unit are interfaced to the control processor and testing processor via two interfacing boards; the Standard Transceiver Board and the ISBX Transceiver Board. These two interface boards permit communication between the two types of buses (STD and ISBX).

The testing processor is an Intel 8086 16-bit microprocessor which has an 8086 central processing unit and 8086 and 8087 math coprocessor boards. The math coprocessor provides all of the data reduction, data correction, and corrections for path length variation and alinearity on the log amplifiers, etc. The system generates a multiplicity of data that needs to be analyzed and precondensed before it can be used. Each chemistry test has a set of software parameter blocks, sequence control blocks, data analysis blocks, etc. This information is used to tell the control processor what type of math is to be used, ratios to be calculated, output data format, and so forth. Since this data is frequently more than what can be transmitted, it must be precondensed in the 8086 microprocessor before it is transmitted. The A/D Converter in the data acquisition unit is capable of making one conversion every 15 microseconds. Since the system can run spectrum scans as fast as 100 milliseconds per scan, the front ends and all of the analog circuitry of the system must be fast. Because of this fast operating speed, certain types of noise cannot be filtered out using hardware, but must be filtered through software using digital-filtering techniques within the 8086 microprocessor.

The system is set up by downloading, to the 8086 central processing unit, everything it needs to run the chemistry tests. As many as 30 such test chemistry processes can be stored by the testing processor 25. The testing processor 25 then provides the control processor 14 a sequence control block that describes the procedure of a test chemistry to be performed. With this control block, the appropriate wavelength is selected; and a multiplicity of readings is taken. This data then goes through digital processing in the 8086 microprocessor. Thus, in a sense, the testing processor 25 tells the control processor 14 what tests it wants to run. The control processor controls all the mechanical operations, collects and then transfers the data to the 8086 memory. The testing processor 25 is then informed that a particular flow cell test is finished. The testing processor 25 then provides the information needed for testing the next flow cell. While the testing is being conducted, the testing processor 25 operates on the data from the earlier tests; and the data is reduced for use.

By downloading the information needed to run any of 30 chemistries, the only system inputs needed are the identification of the tests to be conducted. The system automatically knows what the output format should be. The control processor has all of the alignment tables (i.e., what grating positions to use, what light source intensities to use, what gain ranges to use, etc.) that are needed to run the selected chemistry.

No manual adjustments are needed in the electronics system. The electronic units are processor controlled. Each time the system is turned on, and anytime it is operated, the system will go through its alignment process and flag anything that it finds misaligned or that it cannot align correctly. Thus, if the CRT screen indicates a detected defective data acquisition unit, the user can pull the defective DAU out of the chassis, insert a spare one, and re-initiate the alignment process to automatically align the new DAU. The self-diagnosis of the system can be as specific as detecting a defective log amp, preamp, or a photomultiplier tube that has an improper response. However, there are some areas where human judgment may have to be made. For example, the CRT screen may indicate a bad test photomultiplier tube; but since the PMT is part of the preamp circuitry of the analog processing unit, the defect could be the preamp itself. A new PMT tube can be installed to see if the same error message continues on the CRT screen (process of elimination). If not, the defect is in the preamp circuitry.

With the system, a test can be completed in about 7 seconds on a single index and in about 14 seconds on a double index. Each of the four flow cells can be read in 200 ms for each pass. During that 200 ms, any wavelength or any combination of wavelengths can be selected; multiple scans (reads) can be taken; and as many as 3000 data points per scan can be recorded.

In one test, each flow cell can be scanned five times, yielding 15,000 data points. On a double index test, each flow cell is scanned ten times, yielding 30,000 data points. All of this data is condensed in the 8086/8087 testing processor. Depending upon the chemistry, all of the data can be averaged; or a digital filter of all of the data can be conducted first with a subsequent averaging. Also, 250 different wavelengths can be used in 200 ms per flow cell if needed (i.e., run a full spectrum at one time). This is very advantageous when running a kinetic test, such as seeking how much of the reaction is settling and turbidity, and how much is the actual reaction itself. The system can even determine how much enzyme is turned over into another product. To obtain correct data, the system has the capability to detect bubbles by inspecting the spectrum to determine if there is a bubble present in the flow cell.

Figure 3A:
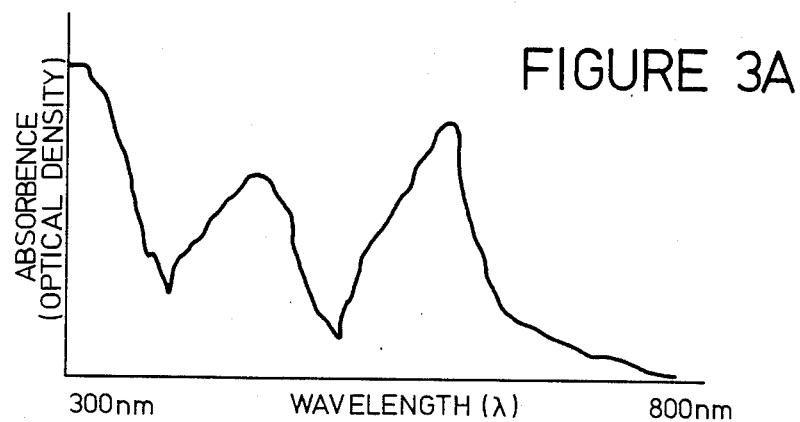
FIG. 3 illustrates hypothetical test results and a serum function and its derivatives.

Such a multiplicity of test data permits the use of mathematical numerical analysis techniques on the data to determine test-solution, light-absorbance characteristics as a function of wavelength. FIG. 3a indicates a hypothetical test chemistry characteristic as a function of wavelength. Such a complex function can be reliably determined with a multiplicity of data points while a few data points will provide little reliable information on the variations of light absorbance as a function of wavelength or the rates of change. By further numerical analysis of the test data, the first and second derivatives of the light-absorbance characteristic can be derived.

Figure 3B:
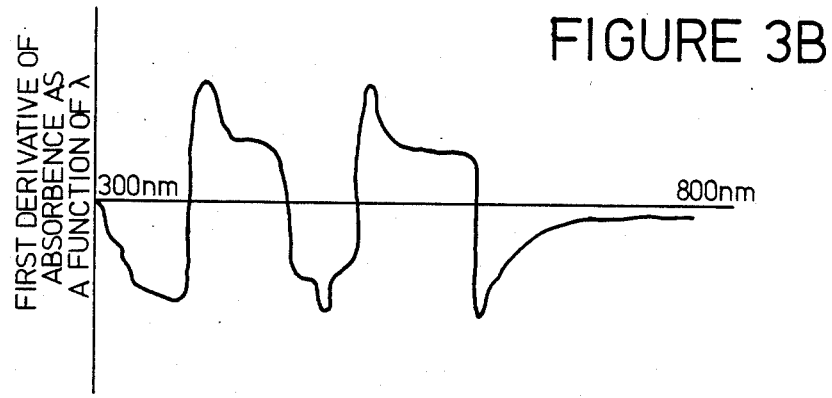
Figure 3C:
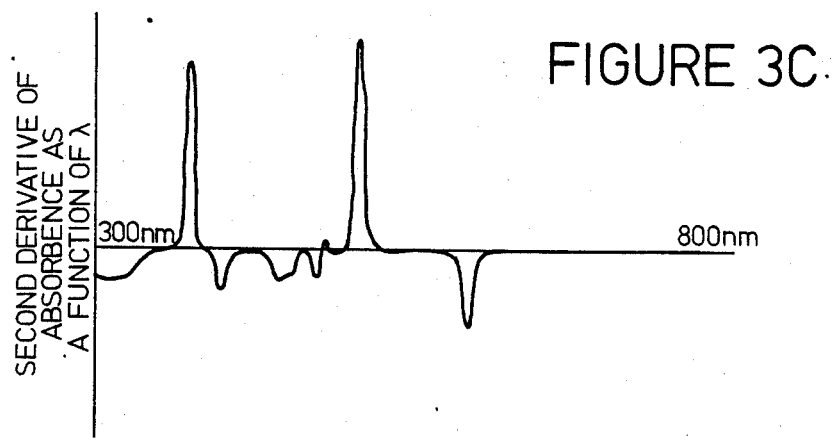

The testing processor can, for example, determine the first and second derivatives of the serum light absorbance as a function of wavelength. FIGS. 3b and 3c indicate, for example, such derived first and second derivatives of the FIG. 3a test solution characteristic. Analysis of the test chemistry for interferences and for faulty tests can permit purification of test chemistry data by subtracting the influence of the interference from the collected data. Higher order derivatives can also be developed and may be usable in such analysis.

Information on the light absorbance of the test solution as a function of wavelength and on the derived first and second derivatives of the test solution data as a function of wavelength can be compared with stored information on the light absorbance characteristics of known interferences as a function of wavelength and on the first and second derivatives of such interference characteristics. The system can thus more reliably check for and identify factors that may interfere with a reliable analysis of the test solution.

Upon the identification of an interfering factor or factors and the level of its or their contributions to the light-absorbance characteristics of the test solution, the test data may be "purified" by subtracting from it a derived estimate of the contribution or contributions of an interference or interferences to the test results. In some tests, interferences may invalidate the test results. This system may be used to determine an invalid test and inform the system user. The system may also be used to inform the system user of the presence and identity of interfering factors in the test chemistries to permit the user to exercise his judgment on the test results and their validity. The stored data on the test solution light-absorbance characteristics may, of course, be presented visually by a CRT or printer, as may the derivatives of the light-absorbance characteristics of the test solutions.

In addition, the multiplicity of data taken in sequential scans at known intervals of time can also permit analysis of the kinetics of the test solution. Such data permits an opportunity to identify interfaces based on their different rates of change in real time. Such analysis joined with analysis of first, second (and possibly higher order) derivatives permits a powerful system in testing human serums.

Where, as in prior automatic serum-testing systems, only a few data points were determined, determination of the serum characteristic function and recognition of interferences with the spectrophotometric measurements of the test chemistry were limited in reliability and scope. The speed of operation and the multiplicity of data points available with the system of this invention permit substantially more reliable test results and a greater variety of tests, among its other advantages. The system and its apparatus is also capable of use with new testing procedures and new serum test chemistries as they may developed.

The preferred system described above may be modified without departing from the scope of the invention as claimed.

I claim:

1. In an apparatus for determining the concentration of a substance of interest in each of a plurality of test solutions, comprising:
   means for supporting a plurality of test solutions to be examined:
   means for passing light through said plurality of test solutions;
   means for detecting said light after being passed through said plurality of test solutions and for generating signals representative of the light-transmittance value of each of said plurality of test solutions; and
   means for analyzing said signals for providing a measure of the concentration of the substance of interest in each of said plurality of test solutions,
   the improvement comprising wherein said means for passing light through said plurality of test solutions includes means for generating a plurality of beams of substantially monochromatic light of different wavelengths from a substantially continuous range of available wavelengths, and means for directing said plurality of plurality of substantially monochromatic light beams of different wavelengths to different ones of said plurality of test solutions, said beam-directing means comprising a plurality of optical pathways for directing said plurality of substantially monochromatic light beams to said plurality of test solutions, and optical multiplexer means for directing each of said plurality of substantially monochromatic light beams of different wavelength to a selected one of said plurality of optical pathways for directing each of the substantially monochromatic light beams of different wavelengths to a selected one of said plurality of test solutions.

2. Apparatus as recited in claim 1 wherein said plurality of optical pathways includes fiber optic means for directing the plurality of substantially monochromatic light beams to said plurality of test solutions.

3. Apparatus as recited in claim 1 wherein said means for generating said plurality of beams of substantially monochromatic light includes means for generating a beam of polychromatic light, grating means in the path of said polychromatic light beam, and means for rotating said grating means for separating said polychromatic light beam into light of different substantially monochromatic wavelengths.

4. Apparatus as recited in claim 1 wherein said means for generating a plurality of beams of substantially monochromatic light includes means for maintaining the intensity of said plurality of substantially monochromatic light beams substantially constant irrespective of the wavelength thereof.

5. Apparatus as recited in claim 4 wherein said means for generating a plurality of beams of substantially monochromatic light includes a light source; and wherein said intensity-maintaining means includes a variable aperture optical system in the path of the light from said light source; and wherein said apparatus further includes means for monitoring said substantially monochromatic light beams, and means responsive to signals from said monitoring means for controlling said variable aperture optical system to maintain the intensity of said substantially monochromatic beams of light constant irrespective of the wavelength thereof.

6. Apparatus as recited in claim 1 wherein the bandwidth of each of said substantially monochromatic light beams is about three nanometers.

7. Apparatus as recited in claim 3 and further including means for calibrating said grating means, said calibrating means, comprising:
a calibration element, said calibration element having a known absorbance for wavelengths of light within the polychromatic light;
means for passing substantially monochromatic light of substantially equal intensities of each wavelength available from said grating through said calibration element in sequence;
means for detecting said light passing through said element and for generating data representative of the absorbance at each available wavelength;
means for comparing said generated data with reference data representing what the absorbance should be for each given wavelength and identifying the wavelength at each rotational position of the grating; and
means for recording the wavelength corresponding to each rotational position of the grating and for controling said means for rotating said grating for providing said light beams of selected substantially monochromatic wavelengths to said plurality of test solutions.

8. Apparatus as recited in claim 7 wherein said calibration element comprises a holmium oxide filter.

9. Apparatus as recited in claim 7 wherein said means for detecting said light passing through said element includes a photomultiplier tube and wherein said means for passing light through said element comprises fiber optic means for directing said substantially monochromatic beam of light at each available wavelength to said photomultiplier tube.

10. Apparatus as recited in claim 3 wherein said polychromatic light beam generating means includes lamp means and filter means in the path of light from said lamp means for passing light of a selected bandwidth to said grating means from said lamp means.

11. Apparatus as recited in claim 10 wherein said selected bandwidth is about 300 nanometers to about 800 nanometers.

12. Apparatus as recited in claim 10 wherein said filter means comprises two order-separation glasses, one of said glasses passing light within a bandwidth of about 300 nanometers to about 500 nanometers, the other of said glasses passing light within a bandwidth of about 400 nanometers to about 800 nanometers, and means for inserting a selected one of said glasses into the path of the light from said lamp means.

13. Apparatus as recited in claim 2 wherein said fiber-optic means includes a plurality of fiber-optic bundles and wherein said optical multiplexer means includes mirror means in the path of said substantially monochromatic light beams from said monochromatic light beam generating means, and a stepper motor connected to said mirror means for moving said mirror means for directing each of the plurality of substantially monochromatic light beams to a selected one of said fiber-optic bundles for directing each of said substantially monochromatic light beams to a selected one of said plurality of test solutions.

14. Apparatus as recited in claim 1 wherein said plurality of test solutions each comprises a mixture of a serum sample and one or more reagents.

15. An automatic method of testing a serum sample which includes the steps of directing a substantially monochromatic beam of light of selected wavelength to a test chemistry of the serum sample being tested, and detecting the intensity of the substantially monochromatic beam of light passing through the test chemistry of the serum sample to provide data on the light-absorbance characteristics of the serum sample, the method further including the steps of
storing first data on the light-absorbance characteristic of the serum sample as a function of wavelength at a multiplicity of selected substantially monochromatic wavelengths;
taking the mathematical first derivative of the light-absorbance characteristic of the serum sample defined by the first data and storing second data on the mathematical first derivative of the first data;
taking the mathematical second derivative of the light-absorbance characteristic of the serum sample defined by the first data and storing third data on the mathematical second derivative of the first data; and comparing the first, second, and third data with stored data on the light-absorbance characteristics of known interferences as a function of wavelength and on the first and second derivatives of such known interferences for analyzing said test chemistry for interferences.

16. The method of claim 15 further including the step of invalidating the test chemistry and providing an operator usable indication of the presence and identity of interferences in the test chemistry.

17. The method of claim 16 further including the steps of analyzing the serum characteristic defined by the first, second, and third data;

comparing the stored first, second, and third data on the light-absorbance characteristic of the serum sample with stored data on the light-absorbance characteristics of one or more interferences to identify any present interferences; and generating interference data and subtracting the generated interference data from the first data to provide more reliable data on the serum sample test chemistry.

18. The method of claim 15 wherein the steps are repeated at a plurality of known intervals and including the step of generating interference data by analysing the first, second, and third data as a function of time at a portion of the multiplicity of selected wavelengths.

19. The method of claim 17 wherein the steps are repeated at a plurality of known intervals, and including the step of developing the serum characteristic as a function of time at a plurality of selected wavelengths.

20. An apparatus for analyzing test chemistries, comparising means for rapidly generating monochromatic light of differing wavelengths over wide spectrum for analyzing test chemistries, means for directing the monochromatic light of differing wavelengths to an intensity monitor, wavelength calibration means and a plurality of test detectors for generating test data on tests taking place in the plurality of test detectors, a test controller for analyzing the test data and a process controller for controlling the process of operation of said apparatus, said process controller and said test controller including means for identifying and storing test data points from said plurality of test detectors at a multiplicity of differing wavelengths, and for identifying and storing the wavelength of the monochromatic light for each of the multiplicity of test data points, said generating means, said directing means, said plurality of test detectors, said intensity monitor, said process controller, and said test controller all responding in real time for generating such a multiplicity of test data that said test controller can develop reliable mathematical derivatives of the test data as a function of wavelength over the entire spectrum.

21. The apparatus of claim 20 wherein said intensity monitor includes means for detecting the intensity of the monochromatic light of differing wavelengths after it has entered and is passing through the directing means to provide a signal to the process controller, the process controller controlling the intensity of the monochromatic light of differing wavelength as it leaves the light-generating means and as it enters the directing means.

22. The apparatus of claim 20 wherein said apparatus generates as many as 3000 test data points for each test chemistry.

23. The apparatus of claim 20 wherein said generating means and directing means direct monochromatic light of differing wavelengths through said test chemistries in said test detectors a plurality of times for each test chemistry and generate a large number of data points each time said light is detected.

24. The apparatus of claim 23 wherein said plurality of times comprises five times.

25. The apparatus of claim 22 wherein said test control includes means for performing mathematical numerical analysis on said test data for analyzing said test data.

26. An automatic apparatus for determining the concentration of a substance of interest in a test solution comprising means for supporting a plurality of test solutions to be examined;

means for passing monochromatic light through said plurality of test solutions;

means for detecting said monochromatic light after being passed through said plurality of test solutions and for generating data representative of the light-transmittance value of said plurality of test solutions; and means for analyzing said data for providing a measure of the concentration in said plurality of test solutions of said substance of interest, said means for passing monochromatic light through said plurality of test solutions including means for rapidly generating a plurality of beams of monochromatic light of different selected wavelengths, each of said beams of monochromatic light being of substantially any desired wavelength within a substantially continuous range of available wavelengths, and means for substantially simultaneously directing said plurality of monochromatic beams of light of different wavelengths to different ones of said plurality of test solutions.

27. The apparatus of claim 26 wherein said directing means includes means for directing substantially monochromatic light of a plurality of different selected wavelengths to each of said test solutions.

28. The apparatus of claim 27 wherein said detecting means includes means for generating a large number of data points representative of the light transmittance value of each of said test solutions at each of the selected substantially monochromatic wavelengths passed through said test solutions; and said analyzing means includes means for analyzing said large number of data points by mathematical numerical analysis techniques to determine light-absorbance characteristics of said plurality of test solutions as a function of wavelength.

29. The apparatus of claim 27 wherein said directing means comprises a plurality of fiber optic bundles and multiplexer means for simultaneously directing the plurality of substantially monochromatic light beams to selected fiber optical bundles for simultaneously directing substantially monochromatic light beams of selected wavelength to selected one of said plurality of test solutions.

30. The apparatus of claim 29 wherein said multiplexer means includes mirror means and means for moving said mirror means to direct the plurality of substantially monochromatic light beams of selected wavelength to selected ones of said fiber optic bundles.

31. An automatic apparatus for determining the concentration of a substance of interest in a test solution comprising:
- means for supporting a plurality of test solutions to be examined;
- means for passing monochromatic light through said plurality of test solutions;
- means for detecting said monochromatic light after being passed through said plurality of test solutions and for generating data representative of the light-transmittance value of said plurality of test solutions; and
- means for analyzing said data for providing a measure of the concentration in said plurality of test solutions of said substance of interest, wherein said analyzing means includes:
- means for storing data on the light-absorbance characteristic of the test solution as a function of wavelength at a multiplicity of selected substantially monochromatic wavelengths;
- means for taking the mathematical first derivative of the light-absorbance characteristic defined by the data and storing data on the mathematical first derivative of the data;
- means for taking the mathematical second derivative of the light-absorbance characteristic defined by the data and storing data on the mathematical second derivative of the data; and
- means for comparing the characteristic defined by the data and the first and second derivatives of the characteristic with stored data corresponding to known interferences.

32. The apparatus of claim 31 further including:
means for analysing the serum characteristic defined by the data and its first and second derivatives;
- means for comparing the stored data on the light-absorbance characteristics of the test solution with stored data on the light-absorbance characteristics of one or more interferences to identify any present interferences; and
- means for generating interference data from the characteristic data to provide more reliable data on the test solution.

* * * * *

UNITED STATES PATENT AND TRADEMARK OFFICE
CERTIFICATE OF CORRECTION

PATENT NO. : 4,669,878
DATED : June 2, 1987
INVENTOR(S) : Daniel J. Meier

It is certified that error appears in the above-identified patent and that said Letters Patent is hereby corrected as shown below:

In col. 12, line 56, delete ":" and insert --;--.

In col. 13, line 5, delete "of plurality".

In col. 15, line 38, after "over" insert --a--.

In col. 16, lines 12-13, delete "control" and insert --controller--.

In col. 16, line 62, delete "one" and insert --ones--.

In col. 18, line 19, after "data" insert --and subtracting the generated interference data--.

Signed and Sealed this

Second Day of February, 1988

Attest:

DONALD J. QUIGG

*Attesting Officer*  *Commissioner of Patents and Trademarks*